United States Patent [19]

Franz et al.

[11] Patent Number: 5,560,926
[45] Date of Patent: Oct. 1, 1996

[54] PROCESS FOR THE PRODUCTION OF AN S-IBUPROFEN-CONTAINING TABLET

[75] Inventors: Hermann Franz, Rossdorf; Hans Peter Weckenmann, Darmstadt, both of Germany

[73] Assignee: Merck Patent Gesellschaft mit beschrankter Haftung, Darmstadt, Germany

[21] Appl. No.: 318,898

[22] PCT Filed: Feb. 1, 1994

[86] PCT No.: PCT/EP94/00280

§ 371 Date: Oct. 7, 1994

§ 102(e) Date: Oct. 7, 1994

[87] PCT Pub. No.: WO94/17793

PCT Pub. Date: Aug. 18, 1994

[30] Foreign Application Priority Data

Feb. 10, 1993 [DE] Germany .......................... 43 03 846.8

[51] Int. Cl.⁶ .................................................... A61K 9/20

[52] U.S. Cl. ........................ 424/464; 424/489; 424/451; 424/452; 424/478

[58] Field of Search ................... 424/464, 478, 424/489; 514/570

[56] References Cited

U.S. PATENT DOCUMENTS

| | | | |
|---|---|---|---|
| 5,200,558 | 4/1993 | Kwan | 562/496 |
| 5,240,712 | 8/1993 | Smith et al. | 424/478 |
| 5,260,337 | 11/1993 | Sims et al. | 514/570 |
| 5,288,507 | 2/1994 | Sims et al. | 424/682 |

*Primary Examiner*—Thurman K. Page
*Assistant Examiner*—William E. Benston, Jr.
*Attorney, Agent, or Firm*—Millen, White, Zelano & Branigan, P.C.

[57] ABSTRACT

The invention relates to a process for the production of a tablet containing S-ibuprofen which rapidly releases the active compound, and to S-ibuprofen-containing tablets prepared by this process.

11 Claims, No Drawings

PROCESS FOR THE PRODUCTION OF AN S-IBUPROFEN-CONTAINING TABLET

BACKGROUND OF THE INVENTION

The invention relates to a process for the production of a tablet containing S-ibuprofen which rapidly releases the active compound.

S-Ibuprofen is the pharmacologically active enantiomer of the ibuprofen racemate. Ibuprofen is a generally known non-steroidal substance having analgesic, antiinflammatory and antipyretic action. It has been shown that the administration only of the S form instead of the racemate represents a significant therapeutic advantage. This is described e.g. in the documents EP-OS 0 267 321 or WO 89/00421.

S-Ibuprofen differs, however, significantly in its physical properties from the racemate, so that substantial difficulties occur in the preparation of solid oral forms when using conventional techniques. The melting point of S-ibuprofen is very low at 52° C., while the racemate melts at 75°–78° C. This makes the use of conventional granulation techniques in the production of granules almost impossible, since owing to the addition of heat which is necessary during drying the active compound starts to melt or sinters. It is known from the literature that ibuprofen which is melted or sintered during processing shows an impaired in vivo bioavailability.

The melting point is a problem even in the production of film-coated tablets containing the highermelting ibuprofen racemate. Thus it is known that the bioavailability is likewise impaired in film-coated tablets which have been coated under excessively hot conditions.

Various administration forms have been described hitherto in the prior art. For example WO 88/02625 describes the production of a soft gelatin capsule which is filled with dissolved ibuprofen. In this case ibuprofen is dissolved in polyethylene glycol. The solubility therein can be further improved by neutralizing ibuprofen partially with alkali solutions, such as potassium hydroxide. This type of administration, however, is not suitable for S-ibuprofen, since either undesirably high decreases in content generally occur as a result of esterification reactions of S-ibuprofen with alcohols in this type of solution of the active compound, or else—which is more serious—racemization of the S-ibuprofen occurs as a result of the addition of potassium hydroxide.

EP-OS 0 299 668 describes the production of hard gelatin capsules by filling with melts. Capsules prepared in this way, however, only dissolve very slowly again, so that this principle is suitable rather for the production of sustained-release forms than of rapid-releasing forms. Melt-embedded materials also count as problematical inasmuch as during storage crystal modifications having altered bioavailability frequently occur.

The conventional matrix tablets claimed in U.S. Pat. No. 5,009,895 are likewise sustained-release formulations which, depending on the mixing ratio of S-ibuprofen to hydroxypropylmethylcellulose employed, lead to tablets whose release is delayed to a highly differing extent.

From the production engineering point of view, the conventional direct tabletting process has the disadvantages that the powder mixture to be compressed flows poorly, the dosing accuracy is inadequate, the tabletting speed is not sufficiently rapid and capping of these tablets cannot be avoided, which in turn makes coating difficult.

SUMMARY OF THE INVENTION

An object of the invention was therefore to find an S-ibuprofen-containing tablet having a rapid delivery of active compound which can be prepared easily on the production scale and which does not have the abovementioned disadvantages.

Surprisingly, it has now been found that by compaction of the powder mixture and, following this, admixture of a dry binder, tablets having the desired advantages can be prepared on the production scale without restrictions.

The invention therefore relates to a process for the production of a tablet containing S-ibuprofen which rapidly releases the active compound, which is characterized in that after the compaction of a powder mixture of active compound and the auxiliaries customary for tablet production further dry binders are additionally admixed to this compactate and this mixture is then compressed again.

The invention furthermore relates to an S-ibuprofen-containing tablet which rapidly releases the active compound and which has been prepared by the process according to the invention.

In the production process according to the invention, the powder mixture consisting of active compound and the auxiliaries customary for tablet production is first compressed in a conventional manner. An additional amount of dry binder is then mixed with this preferably sieved compactate. This mixture is then compressed again.

The obvious solution, the addition of more dry binder to the initial powder mixture, cannot eliminate the disadvantages described. It is all the more surprising that tablets can be prepared on the production scale without any restrictions by the procedure according to the invention.

The further processing of the tablets produced by this process, for example to give film-coated tablets, is then also possible without problems on the production scale using the conventional auxiliaries and processes.

Possible dry binders which according to the invention are additionally admixed to the first compactate are generally known substances such as cellulose powder, microcrystalline cellulose, modified starch or crystalline lactose or alternatively directly tablettable tabletting bases, such as Ludipress® or Cellactose®. Microcrystalline cellulose is preferably employed.

The dry binder in the first compactate and the dry binder then added can be identical or alternatively different.

The amount of the additionally admixed dry binder can be between 4% and 50% (% by weight) relative to the total weight of the tablet. The amount added is preferably between 4 and 25% by weight and an amount between 6 and 10% by weight is particularly preferred.

The tablet base used can be the customary auxiliaries and excipients which are generally known for tablet production to the person skilled in the art and pharmacists. The following substances are preferably used for the powder mixture: talc, starch, microcrystalline cellulose, lactose, highly disperse silica, polyvinylpyrrolidone or cellulose powder. Other constituents are e.g. carbohydrates such as mannitol, kaolin, cellulose and/or derivatives such as methylcellulose, hydroxypropylcellulose, hydroxypropylmethylcellulose, calcium carbonate, calcium or magnesium stearates, and also colorants and/or flavorings.

The amount of the active compound S-ibuprofen can be varied within wide ranges and is preferably between 50 and 600 mg per tablet. Tablets containing 100 mg, 200 mg or 300 mg of S-ibuprofen are particularly preferred.

The amount of the other constituents of the powder base mixture can likewise be varied within a wide range. For example, the following quantitative ranges may be indicated for the production of a preferred powder base mixture:

(The data are percentages by weight and relate to the amount of active compound.)

| | |
|---|---|
| Talc | 2.5–15% |
| Poly(1-vinyl-2-pyrrolidone) | 0.0–10% |
| Highly disperse SiO$_2$ | 2.5–10% |
| Modified starch | 2.5–25% |
| Microcryst. cellulose (Avicel ® PH 102, FMC Corp.) | 0.0–50% |
| Microcryst. cellulose (Avicel ® PH 101, FMC Corp.) | 0.0–50% |

The tablets according to the invention which rapidly release the active compound are produced by sieving the individual constituents of the powder base mixture and the active compound, if necessary, then mixing and then compacting. The sieved compactate is then subsequently mixed again with the appropriate amount of dry binder, if appropriate with addition of talc, and pressed. Adherence to this sequence is essential to the invention.

The tablets produced by this process can be further processed without problems to give film-coated tablets. This further processing can be carried out on the production scale without difficulties using the conventional auxiliaries and techniques. These coating processes are known to the person skilled in the art or are easily accessible from the literature.

As a result of the process according to the invention, for the first time S-ibuprofen-containing tablets can be prepared easily on a production scale without difficulties and without the disadvantages known hitherto and which release the active compound not with a delay but rapidly.

EXAMPLES

Examples 1

Production of a 100 mg S-ibuprofen tablet

| Constituents of the raw tablet: | |
|---|---|
| S-Ibuprofen | 100.00 mg |
| Talc | 3.80 mg |
| Poly(1-vinyl-2-pyrrolidone) ring-opening crosslinked | 4.00 mg |
| Highly disperse silica | 4.80 mg |
| Modified starch | 6.70 mg |
| Microcrystalline cellulose (Avicel ® PH 102) | 26.70 mg |
| Microcrystalline cellulose (Avicel ® PH 101) | 15.00 mg |
| Talc | 5.00 mg |
| Microcrystalline cellulose (Avicel ® PH 101) | 15.00 mg |
| Coating: | |
| Polyethylene glycol 400 | 0.14 mg |
| Talc | 0.45 mg |
| Poly(ethyl acrylate or methacrylic acid) 1:1, 250,000 (Coating dry matter of Eudragit ® L 30 D, Röhm Pharma GmbH) | 0.91 mg |

S-Ibuprofen and highly disperse silica are added through a sieve and premixed for 10 minutes. Avicel PH 102, insoluble polyvinylpyrrolidone, modified starch and also Avicel PH 101 and talc are added to this premixture by sieving through a sieve and mixed for 20 minutes. The mixture is compacted at 50 kN by means of a compactor. The compactate is then taken off by means of a vibratory sieve. The additional Avicel PH 101 and talc are added to these granules by sieving and mixed for 20 minutes. This mixture is then compressed and tabletted using a press force of 4 kN.

Application of the coating:

Polyethylene glycol 400 is dissolved in purified water. Talc is suspended in this solution with stirring. This suspension is slowly stirred into the Eudragit L 30 D dispersion and then sieved. This suspension is then sprayed onto cores prewarmed to about 30° C. The tablets coated in this way are subsequently dried over-night at 30°±5° C.

| Properties: | Raw tablets | Film-coated tablets |
|---|---|---|
| Breaking strength: | 60–110 N | >50 N |
| Disintegration time: | 20–50 seconds | <2 minutes |

Example 2

Film-coated tablets containing 200 mg of S-ibuprofen are produced analogously to Example 1:

| Constituents of the raw tablets | |
|---|---|
| S-Ibuprofen | 4000.0 g |
| Talc | 152.0 g |
| Poly(1-vinyl-2-pyrrolidone) | 160.0 g |
| Highly disperse silica | 192.0 g |
| Modified starch | 268.0 g |
| Avicel ® PH 102 (microcryst. cellulose) | 1068.0 g |
| Avicel ® PH 101 (microcryst. cellulose) | 600.0 g |
| Talc | 200.0 g |
| Avicel ® PE 101 | 600.0 g |
| Coating: | |
| Polyethylene glycol 400 | 5.4 g |
| Talc | 18.0 g |
| Eudragit ® L 30 D (30% coating dry matter) | 122.0 g |
| Purified water | 160.0 g |

The batch size corresponds to 20,000 film-coated tablets.

| Properties: | Raw tablets | Film-coated tablets |
|---|---|---|
| Breaking strength: | 60–110 N | >50 N |
| Disintegration time: | 20–50 seconds | <2 minutes |

Example 3

Analogously to Examples 1 and 2, tablets according to the invention which contain 300 mg of S-ibuprofen are obtained from the following batch.

| Constituents of the raw tablets | |
|---|---|
| S-Ibuprofen | 4050.00 g |
| Talc | 153.90 g |
| Poly(1-vinyl-2-pyrrolidone) | 162.00 g |
| Highly disperse silica | 194.40 g |
| Microcryst. cellulose (Avicel ® PH 102) | 1081.40 g |
| Microcryst. cellulose (Avicel ® PH 101) | 607.50 g |
| Modified starch | 271.35 g |
| Talc | 202.50 g |
| Avicel ® PE 101 | 607.50 g |
| Coating: | |
| Polyethylene glycol 400 | 5.67 g |
| Talc | 18.22 g |
| Eudragit ® L 30 D (30% coating dry matter) | 122.85 g |
| Purified water | 160.0 g |

The batch size corresponds to 13,500 film-coated tablets.

| Properties: | Raw tablets | Film-coated tablets |
| --- | --- | --- |
| Breaking strength: | 60–110 N | >50 N |
| Disintegration time: | 20–50 seconds | <2 minutes |

We claim:

1. A process for the production of a tablet containing S-ibuprofen which rapidly releases active agent, comprising, admixing dry binders to a compacted powder mixture of active agent and customary tabletting auxiliaries and compressing the dry binders with the compacted active agent.

2. The process of claim 1, wherein the amount of the additionally admixed dry binder is 4–50% by weight, relative to the total weight of the tablet.

3. The process of claim 1, wherein the dry binder employed is microcrystalline cellulose or cellulose powder, modified starch or crystalline lactose.

4. The process of claim 1, wherein the powder mixture comprises the following components: S-ibuprofen, talc, highly disperse silica, modified starch and microcrystalline cellulose or optionally crosslinked poly(1-vinyl-2-pyrrolidone).

5. The process of claim 1, wherein a film coating is applied to the tablet after final compressing.

6. An S-ibuprofen-containing tablet which rapidly releases the active compound, produced according to claim 1.

7. Tablet of claim 6, wherein the content of S-ibuprofen is 50 mg to 600 mg.

8. The process of claim 1, wherein the amount of the additionally admixed dry binder is 4–25% by weight, relative to the total weight of the tablet.

9. The process of claim 1, wherein the amount of the additionally admixed dry binder is 6–10% by weight, relative to the total weight of the tablet.

10. A process for the production of an S-ibuprofen containing tablet, said process comprising compacting a mixture of dry binder and a previously compacted mixture of S-ibuprofen and dry binder.

11. A process for the production of an S-ibuprofen containing tablet, said process comprising compacting a mixture of dry binder and a previously compacted mixture of S-ibuprofen, dry binder and customary tabletting auxiliaries.

* * * * *